United States Patent [19]

Hoey

[11] Patent Number: 4,913,853
[45] Date of Patent: Apr. 3, 1990

[54] COMPOSITIONS USEFUL FOR FLUORINE MAGNETIC RESONANCE IMAGING

[75] Inventor: George B. Hoey, St. Louis, Mo.

[73] Assignee: Mallinckrodt, Inc., St. Louis, Mo.

[21] Appl. No.: 940,012

[22] Filed: Dec. 10, 1986

Related U.S. Application Data

[62] Division of Ser. No. 671,456, Nov. 14, 1984, Pat. No. 4,639,634.

[51] Int. Cl.$^4$ ............... C07C 83/00; C07C 91/00; C07C 93/00; C07C 143/74
[52] U.S. Cl. ........................... 562/113; 564/96; 424/9
[58] Field of Search ............ 564/80, 96; 568/16, 568/35; 260/502.4 R, 513 F, 501.17; 424/9

[56] References Cited

U.S. PATENT DOCUMENTS 4,647,447  3/1987  Gries et al. .................. 424/9
4,672,044  6/1987  Schreiber .................... 436/504

OTHER PUBLICATIONS

Nuclear Magnetic Resonance Imaging in Medicine, Kaufman, et al., (editors), Igaku-Shoin, (1982), pp. 197–198.

Sigma Price list, Feb. 1982, p. 678.

Primary Examiner—Robert J. Warden
Assistant Examiner—Richard Wagner
Attorney, Agent, or Firm—Senniger, Powers, Leavitt and Roedel

[57]        ABSTRACT

Water soluble, substantially nontoxic salts of compounds of the formula:

$$CF_3R$$

wherein R is —SO$_3$H, —SO$_2$NH$_2$ or —PO$_3$H$_2$, are useful for obtaining fluorine magnetic resonance images of body organs and tissues. Illustrative salts of such compounds include sodium trifluoromethane sulfonate, N-methylglucaminium trifluoromethanesulfonate and N-methylglucaminium trifluoromethanesulfonamide.

2 Claims, No Drawings

COMPOSITIONS USEFUL FOR FLUORINE MAGNETIC RESONANCE IMAGING

This application is a division of application Ser. No. 671,456, filed Nov. 14, 1984, now U.S. Pat. No. 4,639,365.

BACKGROUND OF THE INVENTION

This invention relates to magnetic resonance imaging (MRI), also referred to as nuclear magnetic resonance (NMR) imaging, and more particularly, to methods and compositions for enhancing magnetic resonance images of body organs and tissues.

The recently developed techniques of MRI or NMR imaging encompasses the detection of certain atomic nuclei utilizing magnetic fields and radio-frequency radiation. It is similar in some respects to x-ray computed tomography (CT) in providing a cross-sectional display of the body organ anatomy with excellent resolution of soft tissue detail. In current use, the images produced constitute a map of the distribution density of protons and/or their relaxation times in organs and tissues. The MRI technique is advantageously non-invasive as it avoids the use of ionizing radiation.

While the phenomenon of NMR was discovered in 1945, it is only relatively recently that it has found application as a means of mapping the internal structure of the body as a result of the original suggestion of Lauterbur (Nature, 242, 190–191, 1973). The lack of any known hazard associated with the level of the magnetic and radio-frequency fields that are employed renders it possible to make repeated scans on vulnerable individuals. Additionally, any scan plane can readily be selected including transverse, coronal, and sagittal sections.

In an NMR experiment, the nuclei under study in a sample (e.g. protons) are irradiated with the appropriate radio-frequency (RF) energy in a highly uniform magnetic field. These nuclei as they relax subsequently emit RF radiation at a sharp resonant frequency. The emitted frequency (RF) of the nuclei depends on the applied magnetic field.

According to known principles, nuclei with appropriate spin when placed in an applied magnetic field [B, expressed generally in units of gauss or tesla ($10^4$ gauss)] align in the direction of the field. In the case of protons, these nuclei process at a frequency $f=42.6$ MHz at a field strength of 1 Tesla. At this frequency, an RF pulse of radiation will excite the nuclei and can be considered to tip the nuclei out of the field direction, the extent of this rotation being determined by the pulse duration and energy. After the RF pulse, the nuclei "relax" or return to equilibrium with the magnetic field, emitting radiation at the resonant frequency. The decay of the signal is characterized by two relaxation times, i.e., $T_1$, the spin-lattice relaxation time or longitudinal relaxation time, that is, time taken by the nuclei to return to equilibrium along the direction of the externally applied magnetic field, and $T_2$, the spin-spin relaxation time associated with the dephasing of the initially coherent precession of individual proton spins. These relaxation times have been established for various fluids, organs and tissues in different species of mammals.

In MRI, scanning planes and slice thickness can be selected without loss of resolution. This permits high quality transverse, coronal and sagittal images to be obtained directly. The absence of any moving parts in MRI equipment promotes a high reliability. It is believed that MRI or NMR imaging has a greater potential than CT for the selective examination of tissue characteristics in view of the fact that in CT, x-ray attenuation coefficients alone determine image contrast whereas at least four separate variables ($T_1$, $T_2$, nuclear spin density and flow) may contribute to the NMR signal. For example, it has been shown (Damadian, Science, 171, 1151, 1971) that the values of the $T_1$ and $T_2$ relaxation in tissues are generally longer by about a factor of 2 in excised specimens of neoplastic tissue compared with the host tissue.

By reason of its sensitivity to subtle physio-chemical differences between organs and/or tissues, it is believed that MRI may be capable of differentiating tissue types and in detecting diseases which induce physio-chemical changes that may not be detected by x-ray or CT which are only sensitive to differences in the electron density of tissue. The images obtainable by MRI techniques also enable the physician to detect structures smaller than those detectable by CT and thereby provide comparable or better spatial resolution.

SUMMARY OF THE INVENTION

Among the several objects of the invention may be noted the provision of compositions useful for obtaining fluorine magnetic resonance images of body organs and tissues; the provision of such compositions which comprise water soluble, substantially nontoxic salts of certain compounds containing trifluoromethyl groups; and the provision of methods for obtaining fluorine magnetic resonance images of body organs and tissues through the administration of such compositions. Other objects and features will be in part apparent and in part pointed out hereinafter.

Briefly, the invention is directed to compositions useful for obtaining fluorine magnetic resonance images of body organs and tissues, the compositions comprising water soluble, substantially nontoxic salts of compounds of the formula:

wherein R is $-SO_3H$, $-SO_2NH_2$ or $-PO_3H_2$. The invention is also directed to methods for obtaining fluorine magnetic resonance images of body organs and tissues by administering such compositions to a mammal in sufficient amounts to provide fluorine magnetic resonance images of the body organs and tissues.

DESCRIPTION OF THE PREFERRED EMBODIMENTS

The evaluation of blood flow and perfusion in tissues by imaging techniques is of physiologic and diagnostic importance. While $^1H$ magnetic resonance imaging has shown some promise for evaluation of blood flow in linear portions of large vessels, no demonstration of tissue perfusion has been made with $^1H$ MRI.

Fluorine atoms ($^{19}F$) give a clear nuclear magnetic resonance signal and thus may function as suitable "probes" in MRI when combined in a chemically suitable form. The specific advantages flowing from the use of $^{19}F$ are: (1) its low intrinsic concentration in soft tissues of the body; (2) its high nuclear magnetic resonance sensitivity, and (3) a magnetogyric ratio which is close to that of $^1H$, thereby making the observation of $^{19}F$ compatible with existing imaging devices.

In accordance with the present invention, it has now been found that the water soluble, substantially nontoxic salts of certain acid compounds containing trifluoromethyl groups are useful as fluorine ($^{19}$F) MRI agents, particularly for use in evaluating blood flow and perfusion. The acid compounds are those of the formula:

CF$_3$R wherein R is —SO$_3$H, —SO$_2$H, —SO$_2$NH$_2$ or —PO$_3$H$_2$, or more specifically, trifluoromethanesulfonic acid, trifluoromethanesulfonamide and trifluoromethanephosphonic acid. Salts of such acid compounds with pharmaceutically acceptable cations conventionally used, for example, in intravenous ionic x-ray contrast agents, such as the sodium, N-methylglucamine and diethanolamine salts, are water soluble and substantially nontoxic and are suitable for use as fluorine MRI agents in the practice of the invention. Solutions of such salts may, for example, be administered intravenously to a mammal in a sufficient amount to provide fluorine images of body organs and tissues by MRI techniques. Illustrative salts of acid compounds containing trifluoromethyl groups which may be used in carrying out the invention include sodium trifluoromethanesulfonate, N-methylglucaminium trifluoromethanesulfonate and N-methylglucaminium trifluoromethanesulfonamide. Other salts of such acid compounds within the purview of the invention may also be employed.

As shown by the studies set forth hereinafter, the fluorine MRI agents of the invention have the ability to detect the lack of myocardial perfusion in a model using coronary arterial ligation. This model produces an infarction of the left ventricle and ventricular septum. Thus, the present invention provides a means for the potential evaluation of perfusion defects.

The following examples illustrate the practice of the invention.

EXAMPLE 1

Preparation of Trifluoromethanesulfonamide

A 2 liter, 3-neck round bottom flask was fitted with a mechanical stirrer and gas feed bubbler (sintered glass type). To the flask was added ether (1.5 l.) and ammonia was bubbled slowly into the ether for approximately 15 min.

Next was added dropwise from an addition funnel trifluoromethanesulfonyl chloride (CF$_3$SO$_2$Cl, 75 ml). The mixture was allowed to stir with the ammonia gas bubbling through it for 2 hours. The reaction mixture was then filtered through a No. 40 Whatman paper. The filtrate was stripped to an oil at 60° C. under vacuum and allowed to sit at room temperature. The semisolid was stirred in toluene (2×250 ml) and the solid filtered off. The tan solid was air dried and weighed 50.37 g.

The solid was dissolved in deionized water (300 ml) and a pH determination made (pH approx. 4). The solution was extracted with chloroform (5×500 ml) and the chloroform extracts stripped to dryness and set aside. The water extract was then stripped to a reduced volume and allowed to cool at room temp. A crystalline solid precipitated and was collected via filtration. This was allowed to air dry overnight. A second crop was collected from the filtrate (mother liquor) and collected in a sintered glass funnel. This was transferred to a tared round bottom flask and combined with material from other similar preparations. This material was sublimed at 62° C. in vacuo (0.06 mm). The resultant white solid was collected in a tared flask and a melting point determination made. M.P. 118°–118.5° C. (sharp).

The results of elemental analysis were as follows:

|   | Calc. | Found |
|---|-------|-------|
| C | 8.06  | 8.05  |
| H | 1.35  | 1.31  |
| N | 9.40  | 9.44  |
| F | 38.25 | 38.42 |
| S | 21.51 | 21.53 |

It was concluded that the desired product, trifluoromethanesulfonamide, was obtained.

EXAMPLE 2

Formulation of N-Methylglucaminium Trifluoromethanesulfonamide

A clean 50 ml Erlenmeyer flask was washed with sterile, deionized water (2×50 ml) and fitted with a magnetic stirrer. To the flask was then added water (10 ml), trifluoromethanesulfonamide (4.0 g) and meglumine (5.24 g, N-methylglucamine). The mixture was stirred at room temperature for 10 minutes. The resultant solution was filtered through a 0.45 Millipore filter, using approximately 1.2 ml of water for injection to complete the transfer. The solution was diluted to 20 ml and transferred to a 50 ml injection vial, and a rubber seal was implaced using a metal crimp cap. The colorless solution had a pH of 7.5–8.0, and was a 1.34M solution 20% w/v trifluoromethanesulfonamide.

EXAMPLE 3

Formulation of N-Methylglucaminium Trifluoromethanesulfonate

Meglumine (120 g, N-methylglucamine) was dissolved in sterile deionized water (300 ml) in a beaker. The beaker was placed in an ice bath and cooled. Trifluoromethylsulfonic acid (100 g) was then slowly pipetted into the beaker in a hood. The pH of the resulting solution was adjusted to approximately 7.0 by the addition of approximately 10 g of N-methylglucamine. The solution was filtered through a 0.45 Millipore filter. The solution was quite viscous and opalescent. The final concentration of N-methylglucaminium trifluoromethanesulfonate was 1.67M.

EXAMPLE 4

Formulation of Sodium Trifluoromethanesulfonate

Trifluoromethanesulfonic acid (17.50 g) was placed in a graduated cylinder and diluted with water (30 ml). The trifluoromethanesulfonic acid was neutralized with 10% sodium hydroxide to a pH of 7.2. The solution was transferred to a rotary evaporator, evaporated to dryness and placed under a vacuum overnight (20.2 g). The sample was collected, ground to a fine powder in mortar and pestle and dried to a constant weight (19.18 g).

EXAMPLE 5

Acute Intravenous Toxicity Determinations of N-Methylglucaminium Trifluoromethanesulfonate and Sodium Trifluoromethanesulfonate Solutions of sodium trifluoromethanesulfonate and N-methylglucaminium trifluoromethanesulfonate were prepared with sterile water for injection, and the pH was adjusted to 7.3–7.4 with either 0.1N HCl or 0.1N NaOH for sodium trifluoromethanesulfonate or 1N meglumine for N-methylglucaminium trifluoromethanesulfonate. The concentration of sodium trifluoromethanesulfonate selected for $LD_{50}$ estimation was 20% w/v, which corresponded to 17.4% free acid, and N-methylglucaminium trifluoromethanesulfonate was also diluted to a concentration of 17.4% free acid for $LD_{50}$ estimation.

A total of 53 Charles River CD-1 Swiss albino mice, 28 male, 25 female, with body weights ranging from 17.9 to 29.8 grams were used. Mice were housed according to standard operating procedures and individually marked with picric acid.

Measured single doses were injected into the lateral tail vein at a rate of 1 ml/min. The animals were observed immediately after dosing and during the 7-day observation period for pharmacotoxic reactions. Recording of terminal body weights and general necrospy of the thoracic and abdominal organs was performed after 7 days. An $LD_{50}$ value was calculated using the method of Litchfield and Wilcoxon (J. Pharmacol. Exp. Ther. 96:99, 1949).

Both compounds caused transient hypoactivity, respiratory depression and stretching and kicking of hind legs. The apparent cause of death was respiratory arrest and all deaths occurred within 1 minute after injection. Surviving mice all gained weight.

The estimated $LD_{50}$ value for sodium trifluoromethanesulfonate, using data from the 17.4% w/v free acid solution, was approximately 2 g free acid/kg of body weight or 40.3 mmol F/kg. An $LD_{50}$ value of 1.92 g free acid/kg or 40.3 mmol F/kg was obtained for N-methylglucaminium trifluoromethanesulfonate.

EXAMPLE 6

Acute Intravenous Toxicity Determination of N-Methylglucaminium Trifluoromethanesulfonamide The procedure of Example 5 was repeated in determining the acute intravenous toxicity of N-methylglucaminium trifluoromethanesulfonate.

Ataxia and hyperactivity followed by hypoactivity were observed within the first hour after dosing at the 5.0, 10.0 and 20.0 mmol/kg dose levels. The degree of hypoactivity increased to moderate-severe during the first 24 hours. Depression, which followed, lasted up to 4 days. Most of the mortalities occurred during this time period. Immediate deaths were observed only at the 40.0 mmol/kg dose level.

At necropsy (end of 7 day observation period), most animals had no abnormalities.

N-Methylglucaminium trifluoromethanesulfonate had an estimated $LD_{50}$ of 15 mmol F/kg. However, deaths were also noted at doses of 5 and 10 mmol/kg ($\frac{1}{4}$ at each level). In addition, there were prolonged toxic reactions (depression and hypoactivity) and deaths were delayed (24 hrs after dosing).

EXAMPLE 7

Magnetic Resonance Imaging of Fluorine During Infusion of N-Methylglucaminium Trifluoromethanesulfonate in Isolated Rabbit Hearts Isolated rabbit hearts were perfused via the coronary arteries in a retrograde fashion. The electrical and contractible functions of the hearts were arrested by perfusion with saturated potassium chloride and subsequently the hearts were perfused with an oxygenated physiological salt solution. The perfusion chamber was placed in a 5 inch bore, 4.2 Tesla magnet with an $R_f$ coil tuned for the magnetic resonance frequency of fluorine. The left anterior descending (LAD) coronary artery was ligated and, 15 minutes later, the perfusion fluid was changed to include N-methylglucaminium trifluoromethanesulfonate (20 mM F, 6.7 mM N-methylglucaminium trifluoromethanesulfonate). Subsequently, MRI cross sectional images of the heart were obtained using fluorine as the imaged nucleus. Those images showed that the rabbit hearts were devoid of fluorine in the region of the left ventricle normally perfused by the LAD, whereas the rest of the myocardium was clearly outlined by the fluorine MR signal.

EXAMPLE 8

In Vivo Spectroscopy in the Rabbit Using N-Methylglucaminium Trifluoromethanesulfonate Anesthetized rabbits (2-4 kg) were placed in a 12 inch bore, 1.9 Tesla MRI magnet. An $R_f$ coil (3.7 cm, I.D., 4 cm, O.D.) was placed over the external surface of the rabbit in the region of the heart, liver or brain. Injections of 2-3 ml of N-methylglucaminium trifluoromethanesulfonate (1.67M, 5.01M in fluorine) were made via catheters inserted into either the external jugular or lateral ear vein. Fluorine MR spectra, consisting of sharp, single peaks (identical to control spectra for solutions of N-methylglucaminium trifluoromethanesulfonate) were observed in the heart and liver as blood carrying the N-methylglucaminium trifluoromethanesulfonate entered those organs. A series of spectra were obtained sequentially in the rabbit heart immediately after an intrajugular vein injection of N-methylglucaminium trifluoromethanesulfonate. In the brain, fluorine spectra appeared to contain two peaks, suggestive of either metabolic transformation of N-methylglucaminium trifluoromethanesulfonate or separation of the compound into two different biological compartments where the fluorine nuclei might behave differently in the magnetic field.

EXAMPLE 9

An anesthetized rabbit was placed in a 12 inch bore, 1.9 Tesla MRI magnet. An $R_f$ coil (3.7 cm, I.D., 4 cm, O.D.) was placed over the external surface of a rabbit in the region of the liver, urinary bladder, or brain. Fluorine spectra were obtained after intravenous injections of 4 mmol F/kg of N-methylglucaminium trifluoromethanesulfonamide (20%, w/v, 1.3M F of N-methylglucaminium trifluoromethanesulfonamide). Fluorine spectra containing large single peaks were observed in liver and brain with smaller peak signal intensities observed in urinary bladder.

At the conclusion of the experiment, the rabbit was killed and heart, liver, kidney, skeletal muscle, spleen, urine and blood samples were analyzed for fluorine by MR spectroscopy. The highest concentrations of fluorine were found in kidney, urine and blood.

EXAMPLE 10

$^{19}F$ images were obtained using a 13 cm bore, 4.25 Tesla magnet with an observe frequency of 167.53 MHz. A small number of rabbit hearts were rapidly excised and perfused using standard techniques. Control hearts were then perfused with a solution of N-methylglucaminium trifluoromethanesulfonate and imaged. Other hearts were subjected to coronary arterial ligation, then perfused with the same solution and imaged.

The images obtained clearly demonstrated differences in perfusion of the myocardium in the infarct model. The control results indicated uniform tissue perfusion. Further, use of gentian violet stain verifies the observed $^{19}$F MRI results.

In view of the above, it will be seen that the several objects of the invention are achieved and other advantageous results attained.

As various changes could be made in the above compositions and methods without departing from the scope of the invention, it is intended that all matter contained in the above description or shown in the accompanying drawings shall be interpreted as illustrative and not in a limiting sense.

What is claimed is:

1. N-Methylglucaminium trifluoromethanesulfonate.
2. N-Methylglucaminium trifluoromethanesulfonamide.

* * * * *